(12) United States Patent
Moszner et al.

(10) Patent No.: US 6,710,149 B2
(45) Date of Patent: Mar. 23, 2004

(54) HYDROLYSIS-STABLE AND POLYMERIZABLE ACRYLOPHOSPHONIC ACID

(75) Inventors: Norbert Moszner, Eschen (LI); André Rumphorst, Vaduz (LI); Volker Rheinberger, Vaduz (LI); Frank Zeuner, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 480 days.

(21) Appl. No.: 09/834,799

(22) Filed: Apr. 13, 2001

(65) Prior Publication Data

US 2002/0016384 A1 Feb. 7, 2002

Related U.S. Application Data

(60) Provisional application No. 60/250,698, filed on Dec. 1, 2000.

(30) Foreign Application Priority Data

Apr. 17, 2000 (DE) .......................... 100 18 968

(51) Int. Cl.[7] .............................. C08F 230/02
(52) U.S. Cl. ................. 526/278; 523/116; 523/118; 558/166; 558/167
(58) Field of Search ............... 523/116, 118; 526/278; 558/166, 167

(56) References Cited

U.S. PATENT DOCUMENTS 4,650,591 A   3/1987   Boothe et al.

FOREIGN PATENT DOCUMENTS

| DE | 27 11 234 B2 | 9/1977 |
|---|---|---|
| DE | 3210775 A1 | 9/1983 |
| DE | 3313819 A1 | 10/1984 |
| DE | 273 846 A1 | 11/1989 |
| DE | 197 46 708 A1 | 4/1999 |
| EP | 0 089 654 A3 | 9/1983 |

*Primary Examiner*—Edward J. Cain
(74) *Attorney, Agent, or Firm*—Nixon Peabody LLP

(57) ABSTRACT

Hydrolysis-stable and polymerizable acrylophosphonic acid with the general formula (I)

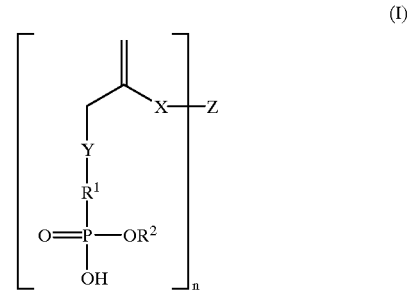

which is particularly suitable as a component of dental materials is disclosed.

11 Claims, No Drawings

HYDROLYSIS-STABLE AND POLYMERIZABLE ACRYLOPHOSPHONIC ACID

This application claims the benefit of U.S. Provisional Patent Application No. 60/250,698, filed Dec. 1, 2000, which is herein incorporated by reference in its entirety.

The present invention relates to polymerizable acrylophosphonic acids which have a high hydrolysis stability and are suitable in particular for preparing, or as components of, polymers, adhesives or other materials and mainly dental materials.

Polymerizable phosphonic acids are of polymer-chemical importance mainly as comonomers. They allow the preparation of organic polymers with high thermal stability, good adhesion properties, high ignition temperature and good solubility in polar solvents. For this purpose, numerous monomeric phosphonic acids with polymerizable vinyl, dienyl, allyl, or styryl groups have been synthetized and polymerized. An overview of phosphonic acids is given by Houben-Weyl, Methoden der Organischen Chemie, Vol. E 20 ($2^{nd}$ part), Georg Thieme Verlag, Stuttgart-New York 1987, p. 1300 et seq). Examples of such conventional polymerizable phosphonic acids are vinyl phosphonic acid, allylbenzene phosphonic acid, α-aminoallyl phosphonic acid, phenylethene phosphonic acid, 1,3-butadiene or isoprene phosphonic acid, 4-vinylbenzene phosphonic acid or 2-(4-vinylphenyl)-ethane phosphonic acid.

Phosphonic acids in which the C=C group is bound to the phosphorus atom directly or via an oxygen atom, such as e.g. vinyl phosphonic acid or ethyl phosphonic acid monovinyl ester, show at most only a moderate tendency towards homopolymerization, so that only homopolymers with a low molecular weight are accessible.

High-molecular-weight polymerisates can on the other hand be obtained from (meth)acrylophosphonic acids or esters in which the (meth)acrylic group is not bound directly to the phosphorus, but via a hydrolysis-stable spacer group. Such (meth)acrylophosphonic acid derivatives are described for example in DE-B-27 11 234.

DE-A-32 10 775 discloses 2-acrylamido-2-methyl-propane phosphonic acid with the formula $CH_2$=CH—CONH—$C(CH_3)_2$—$CH_2$—P(=O)$(OH)_2$ as well as its use for preparing copolymerides.

DE-A-33 13 819 and JP 62-63314 (Chem. Abstr. 107 (1987), 41318f) disclose methacrylic acid-(2-phosphono-1,1-dimethylethylamine) of the formula $CH_2$=$C(CH_3)$—CONH—$C(CH_3)_2$—$CH_2$—P(=O)$(OH)_2$.

According to EP-B-0 089 654 and U.S. Pat. No. 4,650,591 acrylic acid-(2-phosphono-1,1-dimethylethylamine), also called 2-acrylamido-2-methylpropylhosphonic acid, is suitable as a corrosion inhibitor in the form of its homo- or copolymers.

DD-A-273 846 discloses adhesion promoters based on N-acyl-aminomethan-bisphosphonic acid derivatives.

These known (meth)acrylophosphonic acid derivatives are not stable in aqueous solution. Rather, they show, a hydrolytic clearage of the (meth)acrylic group which is even catalyzed by dissociated protons of the phosphonic acid group and thus accelerated.

The use of aqueous solutions is however advantageous in a whole series of applications of polymerizable phosphonic acids. This is the case e.g. in the preparation of low viscosity adhesives which are free from organic solvents, or in dental adhesives which lead to an optimal wetting of the moist dentine surfaces only in aqueous form.

DE 197 46 708 A1 discloses polymerizable acrylophosphonic acids which are hydrolysis-stable in an aqueous solution, have good adhesion properties, can be polymerized with conventional radical initiators and are therefore suitable as a component in particular of adhesives, molded articles, cements or composites and in particular dental materials. The acrylophosphonic acids show a good solubility, in the form of their carboxylic acid esters, in water and polar organic solvents, whereas in the form of carboxylic acids they are easily soluble in water but hardly soluble in organic solvents. The different dissolving behaviour of ester and acid can be disadvantageous in the case of aqueous materials. The hydrolysis of the carboxylic acid esters to produce free carboxylic acid and alcohol can significantly change the solubility of the monomers and thus lead to partial or complete precipitation of the phosphonic acid component and thus influence the properties of the material.

The object of the invention is the preparation of polymerizable acrylophosphonic acids which are practically completely hydrolysis-stable in the presence of water at room temperature.

Surprisingly, this object was achieved by acrylophosphonic acids of the following general formula (I)

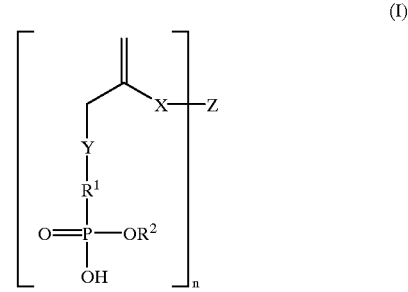

in which $R^1$, $R^2$, $R^3$, X, Y, Z and n have the following meanings:

$R^1$=a linear or branched $C_1$ to $C_{10}$ alkylene or $C_6$ to $C_{14}$ arylene radical;

$R^2$=hydrogen, a linear or branched $C_1$ to $C_{10}$ alkyl or $C_6$ to $C_{10}$ aryl radical;

Y=oxygen, sulphur, $C_1$ to $C_8$ alkylene or is absent;

n=1, 2, 3, 4, or 5;

where

X=CN, n=1 and Z=absent or

X=$CONR^3$ with $R^3$=hydrogen, a linear or branched $C_1$ to $C_{10}$ alkyl radical or a $C_6$ to $C_{10}$ aryl radical;

provided that for n=1

Z=hydrogen or a linear or branched $C_1$ to $C_{10}$ alkyl radical or a phenyl radical; and for n=2 to 5

Z=an aliphatic, aromatic or araliphatic, linear or branched hydrocarbon radical with 1 to 14 carbon atoms, substituted n times with the structure of formula (I) in brackets, when Z and $R^3$ may also be a part of a common ring, and when the individual radicals may be substituted or unsubstituted.

The individual alkyl, aryl, alkylene, arylene, phenyl, phenylene and arylene alkylene radicals can be substituted by one or more substituents, such as Cl, Br, $CH_3O$, OH, COOH, CN, =O, =S, =$NR^2$ or —$NR^3$—CO—C(=$CH_2$) $CH_2$—Y—$R^1$—$PO(OH)_2$.

The nitriles (X=CN) can be transformed into the amides (X=CONR³) and can therefore be regarded as their precursors.

Further, there are preferred definitions for the above mentioned variables of the formula (I) which, unless otherwise stated, can be chosen independently from each other and are as follows:

R¹=a linear or branched C₁ to C₅ alkylene radical or phenylene;

R²=hydrogen or a linear C₁ to C₃ alkyl radical;

Y=oxygen or is absent;

X=CN or CONR³ with

R³=hydrogen, a linear C₁ to C₆ alkyl radical, a phenyl radical or together with Z part of a six-membered ring;

n=1 or 2;

Z=hydrogen or a linear or branched C₁ to C₁₀ alkyl radical, a phenyl radical or together with R³ part of a six-membered ring (for n=1); and Z=a linear C₁ to C₁₀ alkylene radical or together with R³ part of a six-membered ring (for n≧2).

Particularly preferred meanings which can also be chosen independently of each other are:

R¹=a linear or branched C₁ to C₄ alkylene radical;

R²=hydrogen or a methyl radical;

Y=oxygen;

X=CONR³;

R³=hydrogen or a linear C₁ to C₅ alkyl radical;

Z=hydrogen or a linear C₁ to C₆ alkyl radical (for n=1); and

Z=a linear C₁ to C₅ alkylene radical (for n≧2).

The radicals R¹, R², R³ and/or Y are preferably unsubstituted, the radical Z is preferably unsubstituted or substituted by =O, =S, =NR² or —NR³—CO—C (=CH₂)CH₂—Y—R¹—PO(OH)₂.

Preferred compounds are those where at least one, more preferably all, of the variables of formula (I) have the preferred definitions described above, the formula (I) including all the stereoisomers possible through the named substituents and their mixtures, such as racemates.

The acrylophosphonic acids according to the invention of formula (I) (X=CN, Z is absent) can be prepared by reacting alkylphosphonic acid esters APE γ-functionalized at the alkyl radical (R²=alkyl) with α-halogen methylacryl nitrites (U=halogen, preferably Cl or Br) HMAN and subsequent elimination of the alkyl groups R² using methods known from organic chemistry for preparing C—C—, C—O— or C—S— bonds (cf. C. Weygand, G. Hilgetag, Organisch-chemische Experimentierkunst, Johann Ambrosius Bart Verlag, Leipzig 1970, pp. 963 et seq, 362 et seq, and 657 et seq). The protection groups technique is used for the two phosphonic acid groups, i.e. the reactions e.g. are carried out with the corresponding phosphonic acid esters, from which the mono- (R²=alkyl) or dihydrogen phosphonic acids (R²=H) of formula (I) are subsequently released, depending on the hydrolysis reagent used:

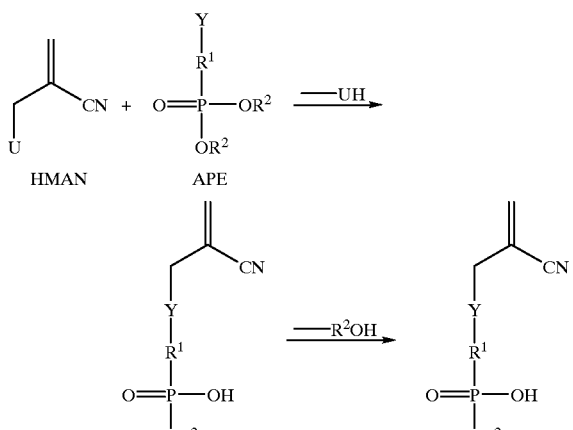

Specifically, the reaction of α-chloromethylacrylnitrile with 2-hydroxyethylphosphonic acid dimethylester via 2-[4-(dimethoxyphosphoryl)-2-oxybutyl]-acrylonitrile gives, after silylation with trimethylsilyl bromide and desilyation with methanol, the corresponding phosphonic acid {2-[4-(dihydroxyphosphoryl)-2-oxabutyl]-acrylonitrile}:

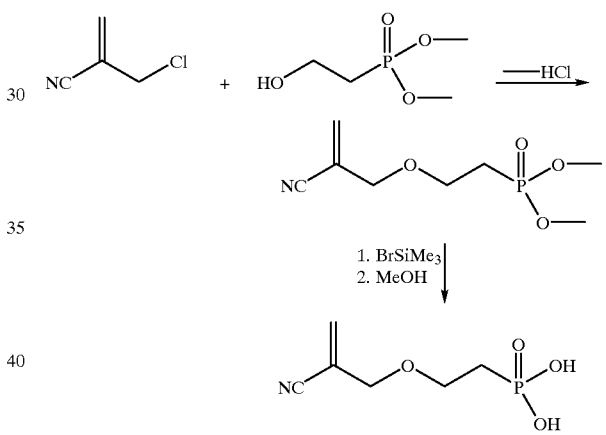

The α-halogen methylacrylonitriles HMAN are accessible by reacting acrylonitrile with formaldehyde in the presence of 1,4-diazabicyclo[2.2.2]octane (DABCO) and subsequent halogenation with inorganic acid chlorides, such as SOCl₂, PCl₃ or PBr₃ (cf. DE-OS 34 44 098 and G. F. Meijs, E. Rizzardo, S. H. Thang, Polym. Bull.24 (1990) 501).

For example, the reaction of acrylonitrile with formaldehyde via α-hydroxymethylacrylonitrile leads, after chlorination with thionyl chloride, to α-chloromethylacrylonitrile:

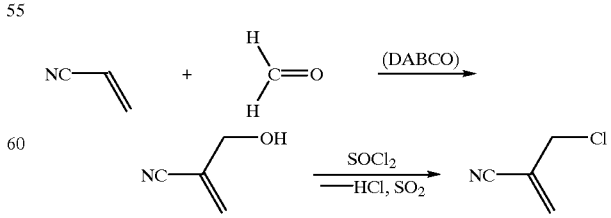

Suitable phosphonic acid esters APE can be obtained in different ways. A particularly suitable reaction for the preparation of alkanephosphohonic acid esters is the Michaelis- Arbuzow reaction (cf. G. M. Kosolapoff, Org. Reactions 6 (1951) 273), where trialkyl phosphites, e.g. triethyl phosphite, and alkyl halides are reacted with each other e.g.:

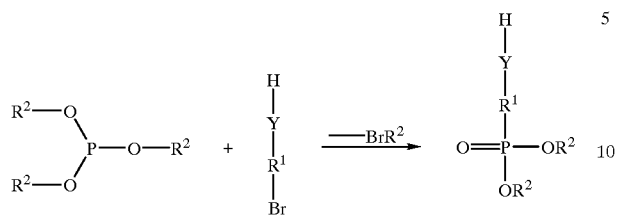

Specifically, upon the reaction of triethyl phosphite with 2-bromoethanol the 2-hydroxyethylphosphonic acid diethyl ester forms:

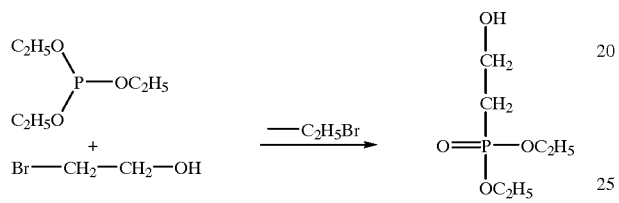

The Y substituent must also be protected where appropriate. A further possibility for the synthesis of hydroxyalkylphosphonic acid esters (YH=OH) comprises the base-catalyzed addition of dialkyl phosphites to mono- or difunctional aldehydes or ketones (F. Texier-Boullet, A. Foucaud, Synthesis, 1982, 916):

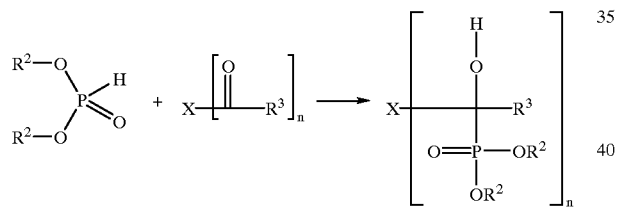

Specifically, as a result of reacting diethyl phosphite with benzaldehyde, (1-hydroxy-1-phenyl)-methylphosphonic acid diethyl ester is obtained:

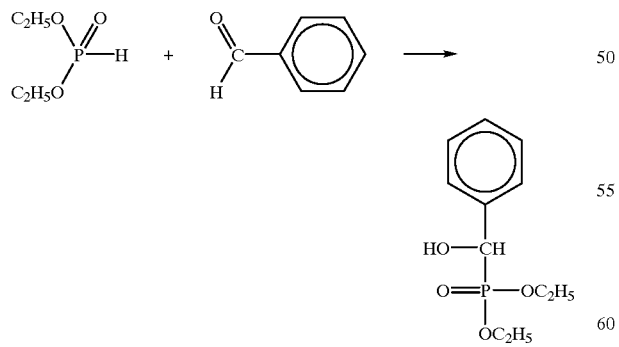

The protection group is preferably eliminated by hydrolytic clearage through silylation with trialkylsilyl halides, e.g. trimethylsilyl chloride/(NaI or NaBr), and subsequent reaction with alcohols or water (S. Freeman, J. Chem. Soc., Perkin Trans. 2, 1991, 263).

The acrylophosphonic acids AP according to the invention of formula (I) ($X=CONR^3$, $n=1$) can be prepared by reaction of dialkoxyphosphoryl acrylic acids DPA with monofunctional amines in the presence of a suitable condensing agent and subsequent hydrolysis of the phosphonic acid ester groups.

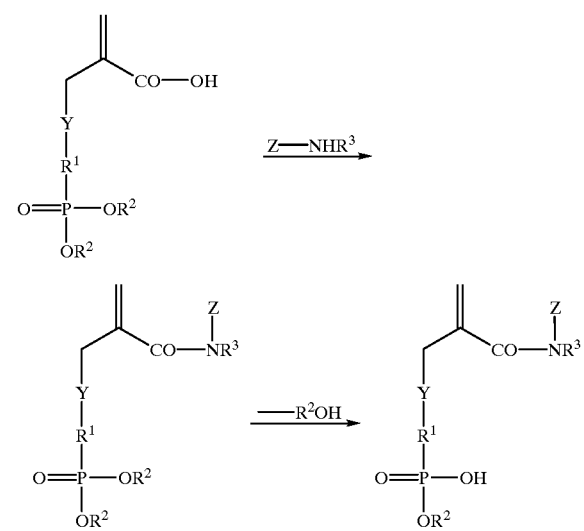

Carbodiimides or phosphoroxychlorides (Houben-Weyl, Vol. 15/2, Peptide; 4$^{th}$ Edition, Georg Thieme Verlag, Stuttgart 1974, pp. 103 et seq and 232 et seq) can be used as condensing agent for the amidation. The elimination of the phosphonic acid ester groups is carried out by means of trimethylsilyl bromide.

By way of example, the reaction of 2-[4-(dimethoxyphosphoryl)-2-oxabutyl]-acrylic acid with diethylamine via 2-[4-(dimethoxyphosphoryl)-2-oxabutyl]-acrylic acid diethylamide gives the corresponding acrylamidophosphonic acid {2-[4-(dihydroxyposphoryl)-2-oxabutyl]-acrylic acid diethylamide}:

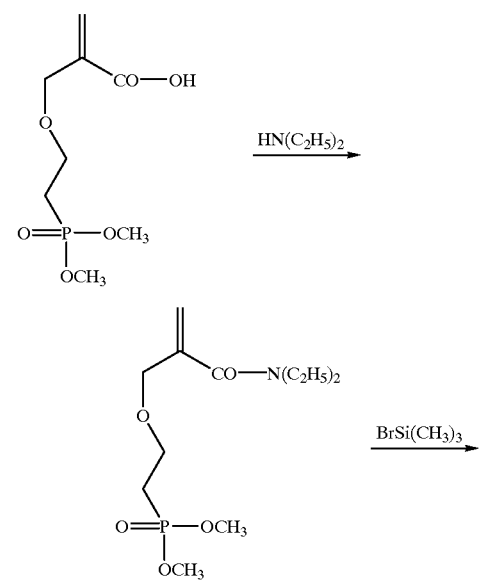

-continued

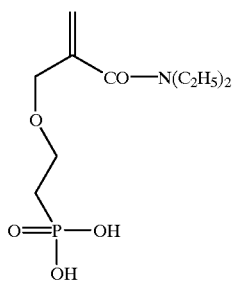

The dialkoxyphosphoryl-acrylic acids DPA used can be prepared from the corresponding dialkoxyphosphoryl-acrylic acid alkyl esters DPAE (cf. N. Moszner, F. Zeuner, U. K. Fischer, V. Rheinberger, Macromol. Chem. Phys. 200 (1999) by selective alkaline hydrolysis, e.g.:

Specifically, the reaction of 2-[4-(dimethoxyphosphoryl)-2-oxabutyl]-acrylic acid ethyl ester with sodium hydroxide with elimination of ethanol gives 2-[4-(dimethoxyphosphoryl)-2-oxa-butyl]-acrylic acid:

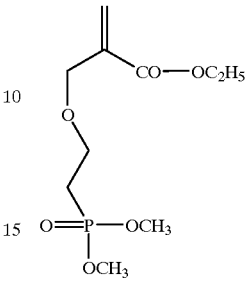 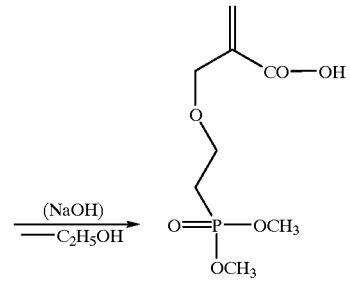

Analogously the amidation of dialkoxyphosphoryl acrylic acids with diamines results in acrylophosphonic acids according to the invention of formula (I) with X=CONR$^3$ and n=2:

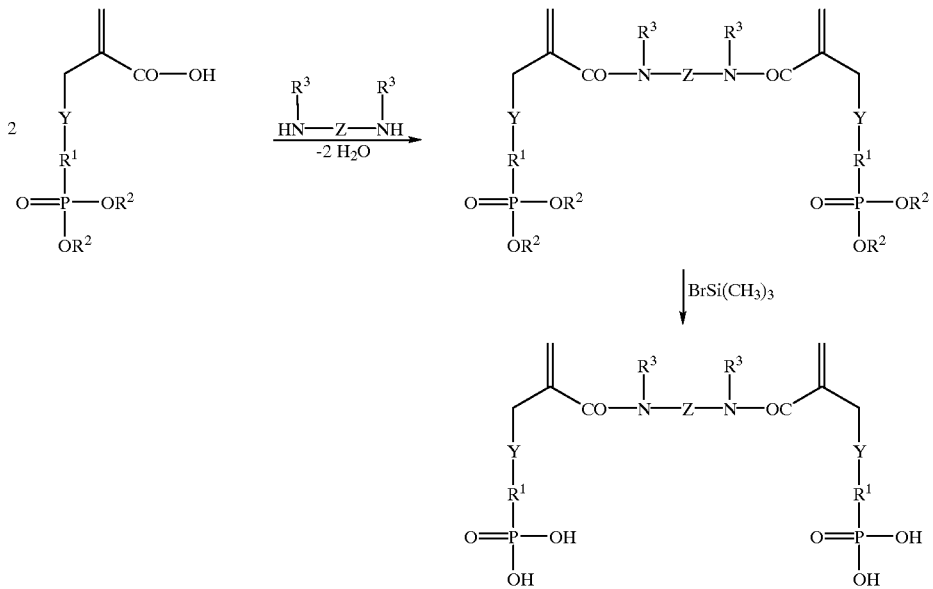

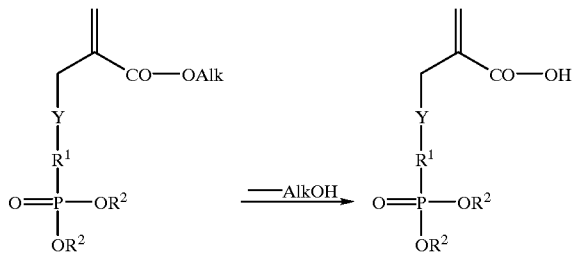

By way of example, the reaction of 2-[4-(dimethoxyphosphoryl)-2-oxa-butyl]-acrylic acid with ethylenediamine gives N,N'-bis-[(6-dimethoxyphosphoryl)-4-oxa-2-methylene-hexanoyl]-ethylenediamine, which can be transformed by treatment with trimethylsilyl bromide into N,N'-bis-[(6-dihydroxyphosphoryl)-4-oxa-2-methylene-hexanoyl]-ethylenediamine:

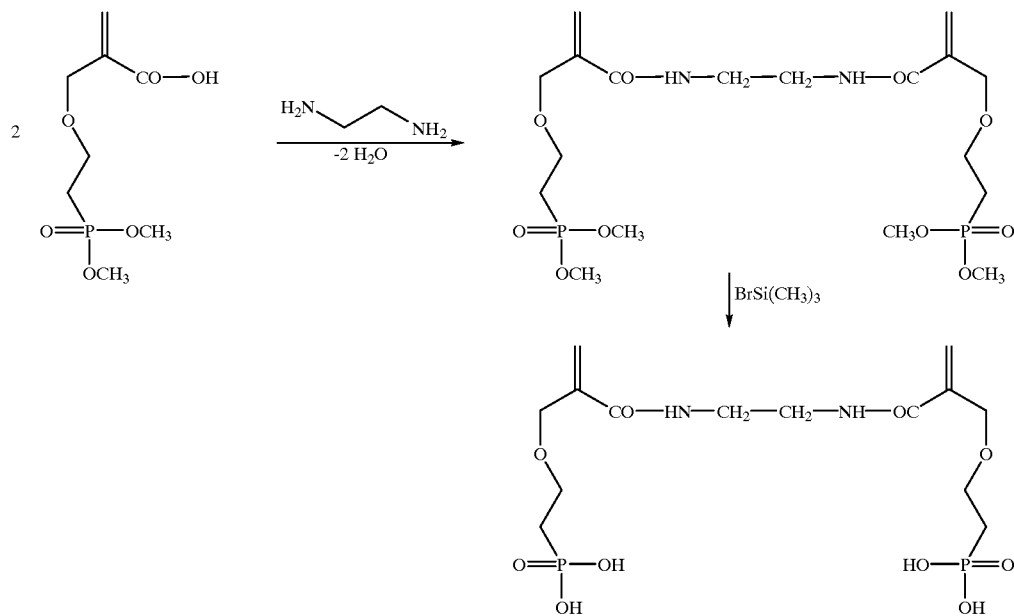
Preferred examples of acrylophosphonic acids according to the invention of formula (I) are i.a.:
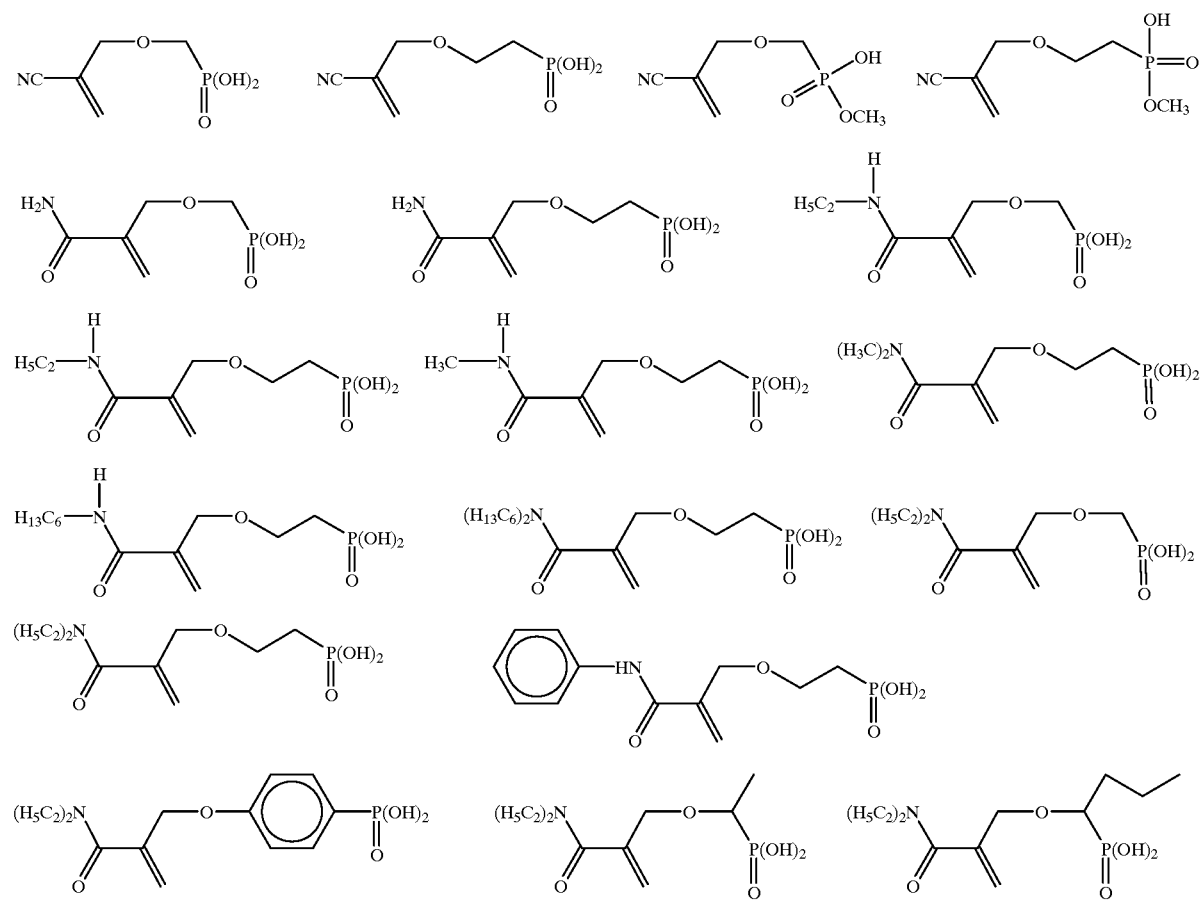

-continued

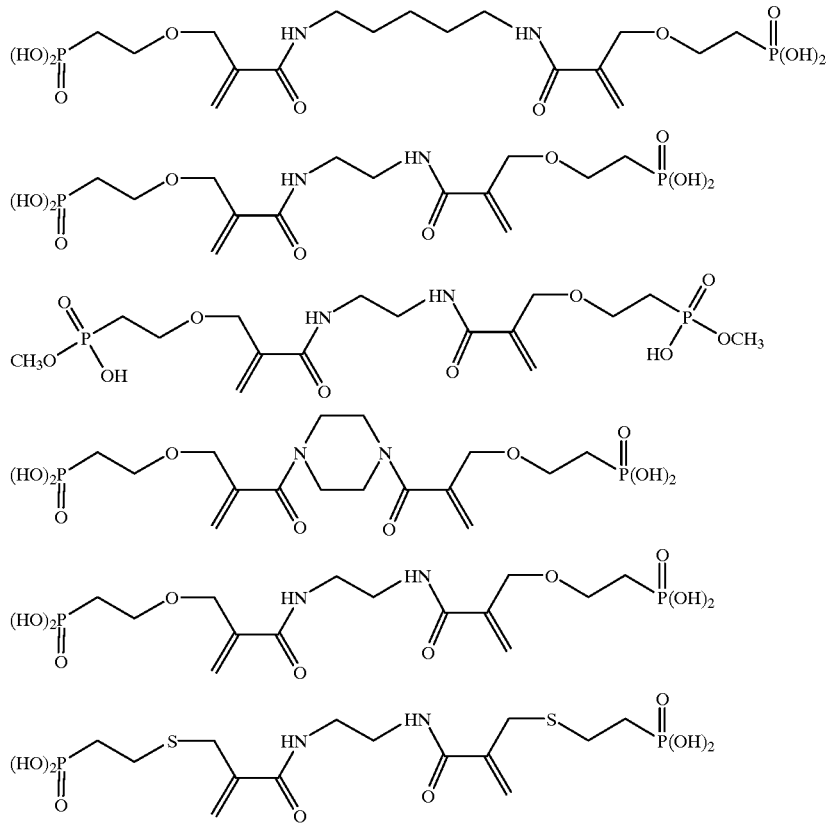

The acrylophosphonic acids according to the invention are practically completely hydrolysis-stable at room temperature. They are therefore suitable in particular for use with aqueous mixtures.

Moreover, the acrylophosphonic acids according to the invention are characterized, compared with the corresponding carboxylic acid derivatives (X=COO, Z=H), by a much better solubility in polar organic solvents such as e.g. ethanol, acetone, methylene chloride or ethyl acetate. In addition, they are largely inert vis-a-vis other compounds such as e.g. organic solvents, while by way of example the corresponding carboxylic acid esters (X=COO, Z—alkyl radical) already have a tendency towards alcoholysis at room temperature in the presence of ethanol.

Due to the presence of polymerizable groups, the acrylophosphonic acid esters according to the invention are suitable as starting materials for the preparation of polymers and copolymers. They can be homopolymerized with the known methods of radical polymerisation or copolymerized e.g. with suitable comonomers.

To carry out the polymerisation, the known radical initiators (cf. Encyclopedia of Polymer Science and Engineering, Vol. 13, Wiley-Interscience Publisher, New York 1988, 754 et seq) can be used. Azo compounds, such as azobis(isobutyronitrile) (AIBN) or azobis-(4-cyanovalerianic acids) or peroxides, such as dibenzoylperoxide, dilauroylperoxide, tert.-butylpercotoate, tert.-butylperbenzoate or di.-(tert.-butyl)peroxide are particularly suitable.

Benzopinacol and 2,2'-dialkylbenzopinacols are also suitable as initiators for hot-curing.

Furthermore, photoinitiators (cf. J. P. Fouassier, J. F. Rabek (Ed.), Radiation Curing in Polymer Science and Technology, Vol. II, Elsevier Applied Science, London and New York 1993) can also be used for polymerisation with UV light or light of visible wavelengths, such as benzoinethers, dialkylbenzilketals, dialkoxyacetophenones, acylphosphinic oxides, α-diketones, such as 9,10-phenanthrenequinone, diacetyl, furil, anisil, 4,4'-dichlorobenzil and 4,4'-dialkoxybenzil, and camphorquinone The acrylophosphonic acids according to the invention can be used in particular as a component of adhesives, cements, composites and molded articles as well as, preferably, dental materials. The compounds according to the invention can also be used in polymerized or partly polymerized form i.e. in the form of polymers such as homo- or copolymers, for example as a component of glass ionomer cements.

The acrylophosphonic acids according to the invention can be polymerized alone or in a mixture with conventional radically polymerizable comonomers, in particular with difunctional crosslinking monomers. Cross-linking bi- or multifunctional acrylates or methacrylates, such as e.g. bisphenol-A-di-(meth)acrylate, bis-GMA (the addition product of methacrylic acid and bisphenol-A-diglycidyl ether), UDMA (the addition product of hydroxyethyl methacrylate and 2,2,4-trimethylhexamethylene diisocyanate), di-, tri- or tetraethylene glycol di(meth)acrylate, trimethylolpropantri(meth)acrylate and pentaerythritol tetra (meth)acrylate above all are suitable for the preparation of adhesives or dental materials. Butane diol di(meth)acrylate, 1,10-decane diol di(meth)acrylate and 1,12-dodecanediol di(meth)acrylate which are accessible by esterifying (meth) acrylic acid with the corresponding diols are also suitable.

The acrylophosphonic acids according to the invention can be used in free form or in the form of their salts, i.e. as phosphonates or phosphonate esters. In case of the alkali-metal ions, in particular sodium and lithium ions, as well as organic ammonium ions, in particular those derived from amine accelerators such as N,N-dihydroxyethyl-p-toluidine, N,N-bis-(2-hydroxy-3-methacryloxypropyl-3,5-xylidine or 4-(dimethylamino)-benzoic acid-2-ethyl-hexylester are preferably used as counterions. Amine accelerators are used in the field of dentistry as a component for example of photoinitiator systems. In general they are tert. amines which can act as H-donators and thus accelerate radical generation (cf. L. A. Linden, "Photocuring of Polymeric Dental Materials and Plastic Composite Resins" in Radiation Curing in Polymer Science and Technology, Vol. IV, J. P. Fouassier, J. F. Rabek (Editors), Elsevier Appl. Sci., London, New York 1993, 396 et seq).

Moreover, the acrylophosphonic acids according to the invention or their mixtures with other radically polymerizable comonomers can be filled with organic or inorganic particles or fibres to improve the mechanical properties. Preferred inorganic particulate fillers are amorphous spherical materials based on mixed oxides of $SiO_2$, $ZrO_2$ and/or $TiO_2$, microfine fillers, such as pyrogenic silicic acid or precipitation silicic acid, as well as macro- or minifillers, such as quartz, glass ceramic or glass powders with an average particle size of 0.01 to 5 μm. Furthermore, x-ray opaque fillers, such as ytterbium trifluoride, or glass fibres, polyamide or carbon fibres can also be used.

If necessary, further components can be added to the acrylophosphonic acids or mixtures thereof, above all solvents, such as water, methanol, ethanol, isopropanol, methyl ethyl ketone, acetone, ethyl acetate, dimethylformamide, dimethyl sulfoxide or mixtures thereof, as well as stabilisers, UV-absorbers, dyes, pigments or lubricants. Water, ethanol, acetone and ethyl acetate as well as mixtures thereof are preferred as solvents for use in dental materials.

The acrylophosphonic acids according to the invention are suitable in particular as a component of dental materials, such as fixing cements and filler composites and above all dental adhesives. Such materials are characterized by a very good adhesion to different substrates, such as hard tooth substance and metallic substrates, and are hydrolysis-stable under moist conditions.

Preferred dental materials according to the invention contain the following components (a), (b), (c), (d) and/or (e):

(a) 0.5 to 99 wt.-%, preferably 10 to 80 wt.-% and particularly preferably 20 to 50 wt.-% of one or more acrylophosphonic acids according to the invention, (b) 0.01 to 5 wt.-% and preferably 0.1 to 2.0 wt.-% of radical initiators, (c) 0 to 80 wt.-%, preferably 0 to 60 wt.-% and particularly preferably 0 to 50 wt.-% radically polymerizable comonomers, (d) 0 to 95 wt.-%, preferably 0 to 80 wt.-% and particularly preferably 0 to 70 wt.-% solvents, in particular water, ethanol, acetone, ethyl acetate or mixtures thereof as well as mixtures of water with the named organic solvents, (e) 0 to 90 wt.-%, particularly preferably, depending on the application, 0 to 20 wt.-% (adhesive), 20 to 60 wt.-% (cement) and 60 to 85 wt.-% (filling composite) filler.

According to a particularly preferred embodiment, the dental materials according to the invention are free from acrylophosphonic acids such as are described by e.g. way of example in DE 197 46 708.

The invention is explained in more detail in the following using examples.

EXAMPLES

Example

Step 1: 2-[4-(dimethoxyphosphoryl)-2-oxa-butyl]-acrylic acid (1)

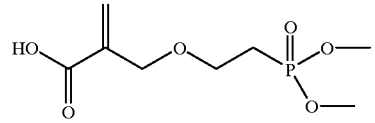

250 ml (0.5 mol) 2 N KOH are added dropwise to 133 g (0.5 mol) 2-[4-(dimethoxyphosphoryl)-2-oxa-butyl]-ethyl acetate, which is accessible by reacting 2-hydroxyethyl-phosphonic acid diethyl ester and α-chloromethylacrylic acid ethyl ester, (cf. N. Moszner, F. Zeuner, U. K. Fischer, V. Rheinberger, Macromol. Chem. Phys. 200 (1999) 1062), so that the temperature remains between −5 and 0° C. Then the reaction mixture is stirred for 2 hours at this temperature and subsequently for another 2 hours at 25° C. The product is washed three times with 250 ml methylene chloride each time, the residual aqueous phase is then adjusted to a pH-value of 1 with concentrated hydrochloric acid and extracted 3 times with 250 ml methylene chloride each time. After the organic extracts have been dried over anhydrous sodium sulphate, they are concentrated on a rotary evaporator and dried at 40° C. in fine vacuum until their weight is constant. 106 g (89% yield) of a colourless, viscous liquid remain, which solidifies after prolonged standing at −18° C.

Elemental analysis:

| | | | |
|---|---|---|---|
| $C_8H_{15}O_6P$: | Calc.: | C 40.34 | H 6.35 |
| (238.18) | Found.: | C 40.24 | H 6.52 |

IR (KBr, $cm^{-1}$): 2958 (s), 1712 (s), 1634 (m), 1455 (m), 1386 (m), 1218 (s), 1180 (s), 1104 (s), 1033 (s), 956 (m), 824 (m), 702 (w), 651 (m).

$^1$H-NMR (400 MHz, $CDCl_3$, ppm): 2.16–2.27 (m, 2H, $CH_2P$), 3.70–3.80 (m, 7H, $CH_3$+$CH_2CH_2O$), 4.21 (S, 2H, C=C—$CH_2O$), 5.92 and 6.37 (s, 2×1H; $CH_2$=C), 10.65 (s, 1H, COOH).

$^{13}$C-NMR (100 MHz, $CDCl_3$, ppm): 22.85 and 24.05 ($CH_2P$), 51.32 ($CH_3$), 62.34 ($CH_2CH_2O$), 66.99 (C=C—$CH_2O$), 124.18 and 134.83 (C=$CH_2$), 166.08 (C=O).

$^{31}$P-NMR (161.9 MHz, $CDCl_3$, ppm): 32.6.

Step 2: 2-[4-(dimethoxyphosphoryl)-2-oxabutyl]-acrylic acid diethylamide (2)

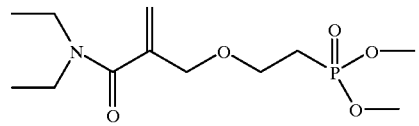

10.2 g (140 mmol) diethylamine are added dropwise at −5° C. to a solution of 35.2 g (148 mmol) 1, 0.5 g (4.1 mmol) 4-dimethylaminopyridine (DMAP) and 8 g hydroquinone monomethyl ether (MEHQ, stabiliser), in 280 ml of anhydrous methylene chloride so that the temperature does not exceed 0° C. Subsequently, 27.0 g (141 mmol) N-(3-dimethylaminopropyl)-N'-ethylcarbodiimide (EDC) are added at the same temperature. After further stirring at room temperature, the reaction mixture is diluted with 420 ml of methylene chloride after 20 hours and then extracted twice, in each case firstly with 2 N NaOH and then with 2 N HCl. Finally, the mixture is washed with saturated NaHCO$_3$ solution and saturated NaCl solution. After the methylene chloride phase has been dried over anhydrous Na$_2$SO$_4$, it is concentrated on a rotary evaporator and the residue is dried at 40° C. and 0.2 mbar until its weight is constant. The fine-vacuum distillation of the obtained raw product resulted in 21.1 g (52% yield) of a bright-yellow oil at boiling point 139° C. (0.08 mbar).

Elemental analysis:

| | | | | |
|---|---|---|---|---|
| C$_{12}$H$_{24}$NO$_5$P: | Calc.: | C 49.14 | H 8.25 | N 4.78 |
| (293.30) | Found.: | C 47.77 | H 8.22 | N 5.02 |

IR (KBr, cm$^{-1}$): 3478 (b), 2972 (m), 1644 (s), 1620 (s), 1462 (s), 1252 (s), 1101 (s), 1032 (s), 947 (m), 821 (s).

$^1$H-NMR (400 MHz, CDCl$_3$ ppm): 1.19 (t, 6H, CH$_3$CH$_2$N), 2.08–2.16 (m, 2H, PCH$_2$CH$_2$O), 3.43 (q, 4H, CH$_3$CH$_2$N), 3.68–3.79 (m, 8H, OCH$_3$ and PCH$_2$CH$_2$O), 4.18 (s, 2H, OCH$_2$C=), 5.19 and 5.39 (s, 2×1H; CH$_2$=).

$^{13}$C-NMR (100 MHz, CDCl$_3$, ppm): 14.36 and 15.06 (CH$_3$CH$_2$N), 25.28 and 26.68 (PCH$_2$CH$_2$O), 38.89 and 42.80 (CH$_3$CH$_2$N), 52.32 (OCH$_3$), 64.63 (PCH$_2$CH$_2$O), 71.64 (OCH$_2$C=), 114.57 (CH$_2$=), 142.22 (C=CH$_2$), 169.81 (C=O).

$^{31}$P-NMR (161.9 MHz, CDCl$_3$, ppm): 31.26.

Step 3: 2-[4-(dihydroxyphosphoryl)-2-oxabutyl]-acrylic acid diethylamide (3)

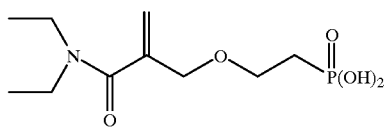

17 g (111 mmol) trimethylsilyl bromide are slowly added dropwise to 13.5 g (51 mmol) of compound 2 and the mixture is subsequently stirred for 2 hours at 40° C. Afterwards, it is firstly concentrated in a water-jet vacuum and then in a fine vacuum (0.2 mbar), 70 ml of absolute methanol are added and the mixture is stirred overnight at room temperature. The slightly yellowish, clear solution is concentrated on the rotary evaporator and dried off in fine vacuum (0.2 mbar) at 40° C. until its weight is constant. 13.5 g (100% yield) of a bight yellow oil remain as product, which has a HPLC purity of 98.1%.

IR (film, cm$^{-1}$): 2975 (s), 2936 (s), 2877 (s), 1570 (s), 1489 (s), 1460 (m), 1317 (m), 1215 (s), 1137 (s), 1010 (s), 944 (s), 790 (w).

$^1$H-NMR (400 MHz, CDCl$_3$ ppm): 1.15 (t, 6H, CH$_3$CH$_2$N), 2.06–2.15 (m, 2H, PCH$_2$CH$_2$O), 3.40–3.45 (m, 4H, CH$_3$CH$_2$N), 3.73–3.80 (m, 2H, PCH$_2$CH$_2$O), 4.17 (s, 2H, OCH$_2$C=), 5.18 and 5.38 (s, 2×1H; CH$_2$=), 11.90 (s, 2H, OH).

$^{13}$C-NMR (100 MHz, CDCl$_3$, ppm): 11.71 and 13.27 (CH$_3$CH$_2$N), 26.42 and 27.80 (PCH$_2$CH$_2$O), 38.56 and 42.39 (CH$_3$CH$_2$N), 64.20 (PCH$_2$CH$_2$O), 70.50 (OCH$_2$C=), 115.05 (CH$_2$=), 140.30 (C=CH$_2$), 170.10 (C=O).

$^{31}$P-NMR (161.9 MHz, CDCl$_3$, ppm): 28.30.

Example 2

Step 1: 2-[4-(dimethoxyphosphoryl)-2-oxabutyl]-acrylonitrile (4)

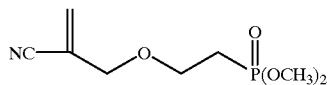

86.3 g (850 mmol) 2-(chloromethyl)-acrylonitrile are added dropwise at room temperature to a solution of 130.9 g (850 mmol) 2-hydroxyethylphosphonic acid dimethylester, 85.9 g (850 mmol) triethylamine (TEA) and 40 mg phenothiazine (stabilizer) in 1 l THF. Subsequently, the mixture is heated for 6 hours at 65° C. under reflux. 9.1 g (90 mmol) TEA and 9.1 g (90 mmol) 2-(chloromethyl)-acrylonitrile are once again added one after the other and the mixture is heated for a further 24 hours under reflux. After the reaction mixture has cooled, the formed deposit of TEA hydrochloride is filtered out and is washed twice with 50 ml THF. After the THF phases have been concentrated on the rotary evaporator, the residual raw product is taken up in 650 ml methylene chloride and washed twice with water. After it has been dried over anhydrous sodium sulphate, the mixture is concentrated and the residual liquid undergoes fractional distillation in the fine vacuum. 101.0 g (54% yield) of a colourless liquid results at b.p. 150° C. (0.05 mbar).

Elemental analysis:

| | | | | |
|---|---|---|---|---|
| C$_8$H$_{14}$NO$_4$P: | Calc.: | C 43.84 | H 6.44 | N 6.39 |
| (219.16) | Found.: | C 43.11 | H 6.98 | N 6.29 |

IR (film, cm$^{-1}$): 2956 (m), 2227 (m), 1626 (w), 1464 (m), 1397 (m), 1250 (s), 1107 (s), 1032 (s), 944 (s), 821 (s).

$^1$H-NMR (400 MHz, CDCl$_3$ ppm): 2.07–2.19 (m, 2H, PCH$_2$CH$_2$O), 3.71–3.83 (m, 8H, OCH$_3$ and PCH$_2$CH$_2$O), 4.11 (s, 2H OCH$_2$C=), 6.06 (s, 2H; CH$_2$=).

$^{13}$C-NMR (100 MHz, CDCl$_3$, ppm): 25.01 and 26.41 (PCH$_2$CH$_2$O), 52.71 (OCH$_3$), 64.58 (PCH$_2$CH$_2$O), 70.03 (OCH$_2$C=), 117.18 (CN), 120.40 (C=CH$_2$), 132.82 (CH$_2$=).

$^{31}$P-NMR (161.9 MHz, CDCl$_3$, ppm): 30.73.

Step 2: 2-[4-(dihydroxyphosphoryl)-2-oxabutyl]-acrylonitrile (5)

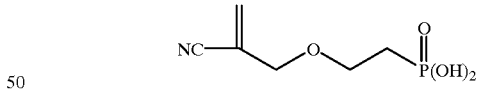

Analogously to the preparation of 3, 55.0 g (250 mmol) 5 were reacted with 84.2 g (550 mmol) trimethylsilyl bromide and worked up. 47.5 g (99% yield) of a dark, wax-like solid resulted.

Elemental analysis:

| | | | | |
|---|---|---|---|---|
| C$_6$H$_{10}$NO$_4$P: | Calc.: | C 37.71 | H 5.27 | N 7.33 |
| (191.12) | Found.: | C 36.15 | H 5.60 | N 7.26 |

IR (film, cm$^{-1}$) 2884 (m), 2228 (m), 1722 (w), 1456 (w), 1398 (w), 1103 (s), 1009 (s), 954 (s).

$^1$H-NMR (400 MHz, CDCl$_3$ ppm): 2.16–2.23 (m, 2H, PCH$_2$CH$_2$O), 3.67–3.81 (m, 2H, PCH$_2$—CH$_2$O), 4.10 (s, 2H, OCH$_2$C=), 6.07 (s, 2H; CH$_2$=), 10.93 (s, 2H, OH).

$^{13}$C-NMR (100 MHz, CDCl$_3$, ppm): 34.06 and 35.96 (PCH$_2$CH$_2$O), 72.04 (PCH$_2$CH$_2$O), 76.90 (OCH$_2$C=), 124.28 (CN), 126.66 (C=CH$_2$), 139.81 (CH$_2$=).

$^{31}$P-NMR (161.9 MHz, CDCl$_3$, ppm): 30.71.

Example 3

Step 1: N,N'-bis-[(6-dimethoxyphosphoryl)-4-oxa-2-methylene-hexanoyl]-1,2-diaminoethane (6)

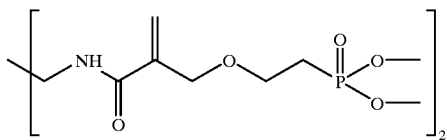

Analogously to the preparation of 2, a solution of 94 g (395 mmol) 1, 1.3 g (10.8 mmol) DMAP and 18 mg MEHQ in 750 ml of anhydrous methylene chloride were reacted at −5° C. with 10.8 g (180 mmol) ethylenediamine and 69.3 g (360 mmol) EDC. After analogous working-up of the reaction mixture, 26.8 g (30% yield) of a yellow oil resulted.

Elemental analysis:

| C$_{18}$H$_{34}$N$_2$O$_8$P$_2$: (500.43) | Calc.: Found.: | C 43.20 C 43.04 | H 6.85 H 6.94 | N 5.60 N 5.52 |
|---|---|---|---|---|

IR (film, cm$^{-1}$): 3322 (m), 2954 (m), 1667 (s), 1622 (s), 1538 (s), 1248 (s), 1104 (s), 1032 (s), 951 (w), 823 (m).

$^1$H-NMR (400 MHz, CDCl$_3$ ppm): 2.07–2.18 (m, 4H, PCH$_2$CH$_2$O), 3.52 (s, 4H, CH$_2$NH), 3.71–3.79 (m, 16H, OCH$_3$ and PCH$_2$CH$_2$O), 4.20 (s, 4H, OCH$_2$C=), 5.59 and 6.06 (s, 2×2H; CH$_2$=), 7.84 (s, 2H, NH).

$^{13}$C-NMR (100 MHz, CDCl$_3$, ppm): 24.88 and 26.28 (PCH$_2$CH$_2$O), 39.57 (CH$_2$NH), 52.45 (OCH$_3$), 64.20 (PCH$_2$CH$_2$O), 7079 (OCH$_2$C=), 123.34 (CH$_2$=), 139.50 (C=CH$_2$), 167.20 (C=O).

$^{31}$P-NMR (161.9 MHz, CDCl$_3$, ppm) 31.74.

Step 2: N,N'-bis-[(6-dihydroxyphosphoryl)-4-oxa-2-methylenehexanoyl]-1,2-diaminoethane (7)

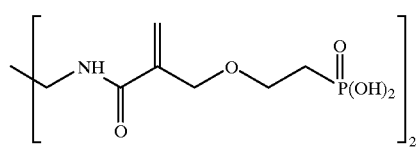

Analogously to the preparation of 3, 11.3 g (22.6 mmol) 6 were reacted with 15.3 g (100 mmol) trimethylsilyl bromide and worked up. 10 g (96% yield) of a redish solid resulted.

IR (film, cm$^{-1}$) 3347 (s, b), 2880 (s), 2318 (m), 1659 (s), 1622 (s), 1609 (s), 1552 (s), 1438 (m), 1362 (m), 1316 (m), 1095 (s), 1002 (s), 935 (s), 715 (m).

$^1$H-NMR (400 MHz, CDCl$_3$ ppm): 1.94–2.02 (m, 4H, PCH$_2$CH$_2$O), 3.34 (s, 4H, CH$_2$NH), 3.50–3.65 (m, 4H, PCH$_2$CH$_2$O), 4.10 (s, 4H, OCH$_2$C=), 4.70 (s, POH+H$_2$O), 5.64 and 6.23 (2s, 2×2H; CH$_2$=).

$^{13}$C-NMR (100 MHz, CDCl$_3$, ppm): 26.95 and 28.29 (PCH$_2$CH$_2$O), 39.05 (CH$_2$NH), 64.66 (PCH$_2$CH$_2$O), 70.24 (OCH$_2$C=), 125.04 (CH$_2$=), 139.39 (C=CH$_2$), 170.32 (C=O).

$^{31}$P-NMR (161.9 MHz, CDCl$_3$, ppm): 26.89.

Example 4

Radical Homopolymerization of Monomers 3 and 5

5.31 g (20.0 mmol) of monomer 3 and 3.82 g (20.0 mmol) of monomer 5 respectively are combined with 2.0 mol-% 2,2'-azobis(isobutyric acid amidine)dihydrochloride and filled up with distilled water to 10 ml monomer solution in a Schlenk-receptacle. The monomer solutions are degassed by multiple repeated freezing under argon and thawing under a fine vacuum and subsequently polymerized under argon at 65° C. During the polymerisation, the viscosity of the starting solution increases perceptibly. After 2 hours, the solutions are precipitated in 10 times the quantity of tetrahydrofuran and dried until its weight is constant. The monomer conversion rate thus gravimetrically established is 23.1% for monomer 3 and 13.7% for monomer 5. The success of the polymerisation can also be confirmed by $^1$NMR spectroskopically.

Example 5

Investigation of the Hydrolytic Stability of Monomers 3 and 5

Monomers 3 and 5 are each dissolved in a 1:1 mixture of water and ethanol and stored as 20% solution at 37° C. The $^1$H-NMR spectrum of the solution is recorded weekly. During the 12-week investigation period, there was no change in the spectrum of monomer 3 or 5, which shows their hydrolytic stability. Under analogous conditions, the monomer 2-[4-(dimethoxyphosphoryl)-2-oxa-butyl]-acrylic acid ethyl ester (comparison monomer 1; X=COO, Z=ethyl) was investigated, a 20% hydrolytic elimination of the ethoxy group being established by $^1$H-NMR spectroscopy after 3 months according to the following equation:

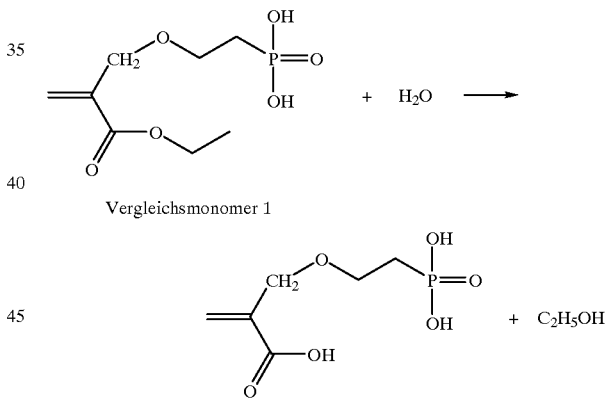

Example 6

Investigation of the Dentine Adhesion of Monomer 3

An adhesive of the following composition (amounts in weight-%) was prepared to examine the dentine adhesion to bovine tooth dentine.

| Monomer 3: | 11.1% |
|---|---|
| Glycerine dimethacrylate: | 11.0% |
| 2-hydroxyethyl methacrylate: | 20.0% |
| Ethanol: | 24.0% |
| bis-GMA: | 33.1% |
| Photoinitiator: | 0.8% |

Bovine teeth are imbedded in plastic cylinders so that the dentine and the plastic are located on one level. After 15 seconds' etching with 37% phosphoric acid thorough rinsing is carried out with water. The dentubili are opened by the acid etching. Then a layer of adhesive of the above composition is painted on with a microbrush, blown on briefly with the air blower to remove the solvent and lit for 40 seconds with a halogen lamp (Astralis 7, Vivadent). A composite cylinder made of Tetric Ceram (Vivadent) is polymerized onto the adhesive layer in two layers of 1 to 2 mm each. Subsequently the testpieces are stored in water for 24 hours at 37° C. and then the adhesive strength is determined. A value of 23.2 MPa was recorded.

Example 7

Investigation of the Adhesion to Enamel of Monomer 5

An adhesive of the following composition (amount in weight-%) was prepared to examine the adhesion to enamel on bovine teeth:

| | |
|---|---|
| Monomer 5: | 11.0% |
| Glycerine dimethacrylate: | 10.0% |
| 2-hydroxyethyl methacrylate: | 20.0% |
| Ethanol: | 25.5% |
| bis-GMA: | 32.7% |
| Photoinitiator: | 0.8% |

Bovine teeth are imbedded in plastic cylinders so that the enamel zone and the plastic are located on one level. After 15 seconds' of etching with a 30% phosphoric acid thorough rinising is carried out with water. Then a layer of adhesive of the above composition is painted on with a microbrush, blown on briefly with the air blower to remove the solvent and lit for 40 seconds with a halogen lamp (Astralis 7, Vivadent). A composite cylinder made of Tetric Ceram (Vivadent) is polymerized onto the adhesive layer in two layers of 1 to 2 mm each. Subsequently the testpieces are stored in water for 24 hours at 37° C. and then the adhesive strength is determined. A value of 15.5 MPa was recorded.

Example 8

Investigation of the Solubility of Monomers 3 and 5

The solubility of monomers 3 and 5 and of a comparison monomer (comparison monomer 2; X=COO, Z=H) in water, ethanol, acetone, methylene chloride and ethyl acetate was investigated. The results are given below.

TABLE 1

Comparison of the solubilities of carbonic acid, carbonic acid amide and carbonic acid nitrile derivatives of acrylophosphonic acid

| ↓Solubility/monomer→ | 3 | 5 | Comparison monomer 2 |
|---|---|---|---|
| water | ++ | ++ | ++ |
| ethanol | ++ | ++ | 0 |
| methylene chloride | ++ | ++ | 0 |
| acetone | ++ | ++ | 0 |
| ethyl acetate | ++ | ++ | 0 |

Solubility: ++: very good (>20 wt.-%), +: good (10–20 wt.-%), 0: practically insoluble (<1 wt.-%).

Vergleichsmonomer 2

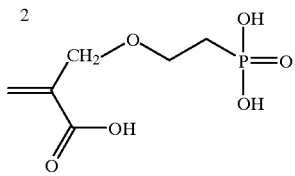

What is claimed is:

1. Acrylophosphonic acid of the general formula (I), stereoisomers thereof or mixtures of these

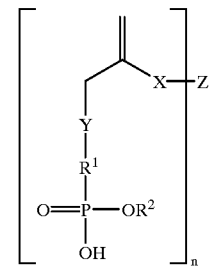

(I)

in which $R^1$, $R^2$, $R^3$, X, Y, Z and n have the following meanings:
  $R^1$=a linear or branched $C_1$ to $C_{10}$ alkylene or $C_6$ to $C_{14}$ arylene radical;
  $R^2$=hydrogen, a linear or branched $C_1$ to $C_{10}$ alkyl or $C_6$ to $C_{10}$ aryl radical;
  Y=oxygen, sulphur, $C_1$ to $C_8$ alkylene or is absent;
  n=1, 2, 3, 4 or 5;
where
  X=CN, n=1 and Z=is absent or
  X=CONR$^3$ with
    $R^3$=hydrogen, a linear or branched $C_1$ to $C_{10}$ alkyl radical, or a $C_6$ to $C_{10}$ aryl radical;
provided that
  for n=1
    Z=hydrogen or a linear or branched $C_1$ to $C_{10}$ alkyl radical, or a phenyl radical; and
  for n=2 to 5
    Z=an aliphatic, aromatic, or araliphatic, linear or branched hydrocarbon radical with 1 to 14 carbon atoms, substituted n times with the structure of formula (I) in brackets, where Z and $R^3$ may also be part of a common ring, and where
the individual radicals may be substituted or unsubstituted.

2. Acrylophosphonic acid according to claim 1, wherein the variables of formula (I) have the following meanings independently of each other:
  $R^1$=a linear or branched $C_1$ to $C_5$ alkylene radical or phenylene;
  $R^2$=hydrogen or a linear $C_1$ to $C_3$ alkyl radical;
  Y=oxygen or is absent;
  X=CN or CONR$^3$ with
    $R^3$=hydrogen, a linear $C_1$ to $C_6$ alkyl radical, a phenyl radical or together with Z part of a six-membered ring;
  n=1 or 2; and
  Z=hydrogen or a linear or branched $C_1$ to $C_{10}$ alkyl radical, a phenyl radical or together with $R^3$ part of a six-membered ring (for n=1); or Z=a linear $C_1$ to $C_{10}$ alkylene radical or together with $R^3$ part of a six-membered ring (for n=2).

3. Acrylophosphonic acid according to claim 2, wherein the variables of formula (I) have the following meanings independently of each other:

$R^1$=a linear $C_1$ to $C_4$ alkylene radical;

$R^2$=hydrogen or a methyl radical;

Y=oxygen;

X=$CONR^3$;

$R^3$=hydrogen or a linear $C_1$ to $C_5$ alkyl radical; and

Z=hydrogen or a linear $C_1$ to $C_6$ alkyl radical (for n=1); or

Z=a linear $C_1$ to $C_5$ alkylene radical (for n=2).

4. Acrylophosphonic acid according to claim 1, wherein the radicals $R^1$, $R^2$, $R^3$ and/or Y are unsubstituted.

5. Acrylophosphonic acid according to claim 1, wherein the radical Z is unsubstituted or is substituted by =O, =S, =$NR^2$ or —$NR^3$—CO—C(=$CH_2$)$CH_2$—Y—$R^1$ PO(OH)$_2$.

6. Acrylophosphonic acid according to claim 1, wherein said acrylophosphonic acid is a component of an adhesive, of a polymer, of a composite, of a cement, of a molded article or a dental material.

7. Acrylophosphonic acid according to claim 6, wherein the dental material is a dental adhesive, a fixing cement or a filling composite.

8. Acrylophosphonic acid according to claim 6, wherein the acrylophosphonic acid is present in at least partially polymerized form.

9. Dental material containing an acrylophosphonic acid according to claim 1.

10. Dental material according to claim 9, containing the acrylophosphonic acid in at least partially polymerized form.

11. Polymers and copolymers obtained by polymerization or copolymerization of an acrylophosphonic acid according to claim 1.

* * * * *